United States Patent
Krytenberg

(10) Patent No.: US 12,240,992 B2
(45) Date of Patent: Mar. 4, 2025

(54) AQUEOUS SILICONE ELASTOMERS AS ROOF COATINGS

(71) Applicant: Industrial Control Development, Inc., Ridgefield, WA (US)

(72) Inventor: Timothy Krytenberg, Ridgefield, WA (US)

(73) Assignee: Industrial Control Development, Inc., Ridgefield, WA (US)

( * ) Notice: Subject to any disclaimer, the term of this patent is extended or adjusted under 35 U.S.C. 154(b) by 0 days.

(21) Appl. No.: 17/521,285

(22) Filed: Nov. 8, 2021

(65) Prior Publication Data
US 2022/0145126 A1 May 12, 2022

Related U.S. Application Data

(60) Provisional application No. 63/112,519, filed on Nov. 11, 2020.

(51) Int. Cl.
*C09D 183/04* (2006.01)
*C09D 5/02* (2006.01)
*C09D 7/20* (2018.01)
*E04D 7/00* (2006.01)

(52) U.S. Cl.
CPC ........... *C09D 183/04* (2013.01); *C09D 5/021* (2013.01); *C09D 7/20* (2018.01); *E04D 7/00* (2013.01)

(58) Field of Classification Search
CPC ........ C09D 183/04; C09D 7/20; C09D 5/021; E04D 7/00
See application file for complete search history.

(56) References Cited

U.S. PATENT DOCUMENTS

| | | | |
|---|---|---|---|
| 3,996,396 A * | 12/1976 | Hansen | E04D 7/00 156/305 |
| 4,535,109 A * | 8/1985 | Kondo | C04B 41/009 524/588 |
| 9,523,022 B2 | 12/2016 | Johnson et al. | |
| 9,828,523 B2 | 11/2017 | Johnson et al. | |
| 10,577,801 B2 | 3/2020 | Tselepis | |
| 2013/0040073 A1 | 2/2013 | Pett et al. | |
| 2020/0181911 A1 | 6/2020 | Tselepis | |

FOREIGN PATENT DOCUMENTS

| | | |
|---|---|---|
| EP | 0 073 564 | 3/1983 |
| EP | 1 169 223 | 1/2006 |

OTHER PUBLICATIONS

International Search Report and Written Opinion issued for International Application No. PCT/US2021/058426 on Feb. 24, 2022.

* cited by examiner

*Primary Examiner* — Robert S Walters, Jr.
(74) *Attorney, Agent, or Firm* — Klarquist Sparkman, LLP

(57) ABSTRACT

A method including coating a liquid aqueous silicone elastomer-containing composition onto a surface of a building roof substrate, wherein the building roof substrate is an element of a standing building roofing system, and then drying the liquid aqueous silicone elastomer-containing composition resulting in forming a topcoat on the building roof substrate.

22 Claims, No Drawings

AQUEOUS SILICONE ELASTOMERS AS ROOF COATINGS

CROSS REFERENCE TO RELATED APPLICATIONS

This application claims the benefit of U.S. Provisional Application No. 63/112,519, filed Nov. 11, 2020, which is incorporated herein by reference in its entirety.

BACKGROUND

Current commercial roofing systems can be grouped into the following classifications: single-ply membranes, spray polyurethane foam, and bituminous.

Single-ply membranes are sheets of rubber such as thermoplastic polyolefin (TPO) or ethylene propylene diene terpolymer (EPDM) which are ballasted, mechanically fastened, or chemically adhered to a roof. While lightweight, the seams between sheets are vulnerable to leaking, and the membranes are easily damaged.

Spray polyurethane foam (SPF) is an expanding polyurethane foam which is sprayed onto the roof, creating a continuous film which provides thermal insulation and waterproofing. A topcoat is required to protect the foam from degradation by sunlight as the polyurethane is not UV stable. Any damage to the topcoat creates potential leaks as the SPF degrades rapidly when exposed to sunlight. SPF roofs require specialized contractors to install and need regular maintenance to prevent failures.

Bituminous systems include Built-Up Roofs (BUR) and asphalt emulsions. BUR are composed of layers of asphalt and reinforced with fabric. They are often followed with a white or silver topcoat to reduce solar heat gain and to protect the asphalt from UV degradation. Asphalt is hot applied which generates hazardous fumes during installation, and the many layers can add weight to a roof.

Asphalt emulsion roofing is an improvement on the traditional Built-Up Roofing Systems. Asphalt emulsion roofs are composed of layers of asphalt reinforced with fabric or glass fibers, and also followed with a white or silver elastomeric topcoat to reduce solar heat gain of the building. Asphalt emulsions are cold applied and do not generate as many fumes as hot applied asphalt roofs. Bituminous roofing systems are advantageous over other systems as they form continuous monolithic films with no seams and are not as vulnerable to mechanical damage. However bituminous systems grow brittle over time as the asphalt ages, due to oxidation of the asphalt and loss of oils. Building movement due to thermal expansion and contraction will create leaks as the brittle asphalt is unable to match the building's movement and will crack.

As such there remains a need for a roofing system which comprises a continuous monolithic film, is durable against physical damage, and remains elastomeric to accommodate building movement.

SUMMARY

Disclosed herein is a method comprising:
onsite coating a liquid aqueous silicone elastomer-containing composition onto a surface of a building roof substrate, wherein the building roof substrate is an element of a standing building roofing system, and
then drying the liquid aqueous silicone elastomer-containing composition resulting in forming a silicone elastomer-containing topcoat on the building roof substrate.

Another embodiment disclosed herein is a method comprising:
onsite coating a liquid aqueous silicone elastomer-containing composition onto a surface of a building roof substrate, wherein the building roof substrate is an element of a standing building roofing system, and
then drying the liquid aqueous silicone elastomer-containing composition to form a membrane on the building roof substrate.

The foregoing and other objects, features, and advantages will become more apparent from the following detailed description.

DETAILED DESCRIPTION

Described herein is the use of an aqueous silicone elastomer-containing composition in coatings for a roof, or a portion thereof, of a building. The silicone-containing composition is directly applied to a roof substrate surface as a sprayable, brush-coatable, or roller-coatable liquid. The silicone-containing composition liquid is not applied to, or impregnated into, a physically separate substrate (e.g., a mesh or a fabric) prior to coating the roof substrate.

In certain embodiments, the aqueous silicone elastomer is an elastomeric topcoat over a roof substrate present in a roofing system. In other embodiments, the aqueous silicone elastomer is a complete, standalone, roofing system. In certain embodiments, a water resistant barrier is not required underneath the silicone coating. The aqueous silicone elastomer can be used as the sole binder in the coating composition, meaning that the aqueous silicone elastomer does not have to blended with another binder.

In certain embodiments, the coating disclosed herein is applied onsite to a standing building roofing system and forms an element of the roofing system. In certain embodiments, the standing building roofing system may be a pre-existing system on a standing building that is undergoing renovation or weatherization. For example, the coating, and resulting membrane, disclosed herein may be used during repair and/or resurfacing of the entire roof over the pre-existing roofing system of a standing building roofing system. In certain embodiments, the standing building roofing system is a roofing system that has been installed on a newly-constructed building.

The silicone elastomer-containing coating exhibits advantageous weather resistance, water resistance, flexibility and elongation even at temperature extremes. Compared to an asphalt coating, the silicone elastomer-containing coating displays much greater elongation and a higher tensile strength, even at temperatures as low as −20° C. For example, the silicone elastomer-containing coating can have a percent elongation of at least 500%, more particularly at least 700%, at ambient temperature. The silicone elastomer-containing coating can have a percent elongation of at least 500%, more particularly at least 700%, at −20° C. The silicone elastomer-containing coating can have a tensile strength of at least 500 psi, more particularly at least 600 psi, at ambient temperature. The silicone elastomer-containing coating can have a tensile strength of at least 500 psi, more particularly at least 600 psi, at −20° C.

The silicone elastomer-containing coating also displays much greater weather and UV stability when tested in QUV accelerated weatherometer when compared to an asphalt coating. For example, the silicone elastomer-containing coating can have a mass retention of at least 95%, more particularly at least 97%, over a period of 2000 hours QUV. The silicone elastomer-containing coating can have a gloss retention of at least 90%, more particularly at least 95%, over a period of 2000 hours QUV. The silicone elastomer-containing coating can have a color loss of less than one ΔE over a period of 2000 hours QUV.

The improved weather resistance and physical properties minimizes the potential for roof failure due to building movement or physical damage to the roofing system from regular use and maintenance. It is also beneficial for the roofing system to retain its physical properties under extreme cold for regions that regularly experience harsh winters.

Additionally, the silicone elastomer-containing composition is naturally clear, unlike asphalt or some membranes like EPDM, which are only available in black. The naturally clear composition allows for the option of formulating the silicone elastomer-containing composition to any desired color by adding color additives to the composition. For example, a white silicone elastomer-containing coating so formulated would eliminate the need for a white topcoat to obtain a "cool roof".

Aqueous Silicone Elastomer and Compositions Containing the Elastomer

The aqueous silicone elastomer can be any silicone that forms an elastomer in an aqueous system. Several illustrative aqueous silicone elastomers are described below.

In a first embodiment, an aqueous silicone elastomer may be manufactured with cyclic monomer(s) as a starting reactant via ring-opening polymerization. This method uses cyclic siloxane monomer(s) such as hexamethylcyclotrisiloxane (D3), octamethylcyclotetrasiloxane (D4), or decamethylcyclopentasiloxane (D5). They differ only in the number of siloxane units in the ring. D3 has three siloxane units, D4 has four, and D5 has five. D4 is the most commonly used cyclic for ring-opening-polymerization (ROP).

The cyclic monomers are polymerized by a strong acid catalyst that also functions as an emulsifying agent, known as a surfcat. A surfcat is typically any sulfuric or sulfonic acid, or a salt thereof, that includes a fatty acid or fatty ester moiety. Illustrative surfcats include dodecylbenzenesulfonic acid, sodium lauryl sulfate, sodium olefin sulfonate and sodium dioctyl sulfosuccinate. If the surfcat is in the acid form, it can be used as is. If it is neutralized to form a salt, then the acid form of the catalyst must be regenerated using another strong acid like HCl or $H_2SO_4$. Surfactants other than the surfcat may be used (optional), such as non-ionic surfactants or anionic surfactants that are not strong acids.

The cyclic monomer and the surfcat are emulsified together with water and any optional surfactants or optional crosslinkers. If the salt form of a surfcat is used (such as sodium lauryl sulfate) then the acid form of the surfcat is regenerated by adding in a stronger acid like HCl or $H_2SO_4$. The emulsion is then allowed to polymerize either ambiently or by heating the mixing vessel to 60° C.-90° C. This ring-opens the cyclic monomer and chain extends, creating very high molecular weight linear polydimethylsiloxane. For example, the polydimethylsiloxane may a molecular weight of 250,000-500,000 g/mol.

In certain embodiments, 85-90% of the cyclic monomers are converted into a linear polydimethylsiloxane, and the polymerization can take as long as three weeks under ambient conditions.

Optionally, a crosslinking agent such as a silane or colloidal silica may be added during polymerization.

The surfcat is then neutralized to halt polymerization by adding in a base. This can be any base such as an amine, a metal hydroxide, or a metal carbonate.

The emulsion is then converted from an emulsion of silicone oil to a dispersion of silicone rubber via crosslinking by adding in a filler like colloidal silica, a crosslinker like a silane (optional), and an organotin catalyst. Methyltrimethoxysilane is a preferred silane. The organotin catalyst can be either a divalent tin or a tetravalent tin catalyst. The divalent tin catalyst may be any organotin with a 2+ oxidation state and organic ligands. Examples include tin(II) ethylhexanoate, tin(II) acetylacetonate, and tin(II) acetate. The tetravalent tin catalyst may be any organotin with a 4+ oxidation state, two covalently bonded organic groups and two ligands. Examples include dibutyltindilaurate, dibutyltindiacetate, and dioctyltindilaurate.

The resulting product is an aqueous dispersion of cross-linked polydimethylsiloxane. In certain embodiments, the resulting product is a dimethyl siloxy silsesquioxane. In certain embodiments, the resulting product has a molecular weight of 100,000 to 500,000 g/mol. In certain embodiments, the resulting product has a solids content of 30-70 wt %, preferably 40-60%. In certain embodiments, the resulting product may have a viscosity of 100 cPs to 10000 cPs, preferably 100 to 500 cPs, at 23° C.

In a second embodiment, an aqueous silicone elastomer may be manufactured via linear monomer(s) as a starting reactant. In this embodiment, the starting material is a linear polydimethylsiloxane which are terminated with silanol groups (Si—OH) which allow for polymerization via acid catalyzed condensation. These silanol fluids are classed based on their viscosity, and the most useful for this polymerization method are those in the 1-200 cPs range at 23° C.

This embodiment may include an optional crosslinking agent as in the ROP method described above.

This embodiment also uses a surfcat as in the ROP method described above. Other surfactants such as non-ionic surfactants, etc. may optionally be used in addition to the surfcat.

The silanol fluid, any optional ingredients, the surfcat, and water are emulsified together. If the salt form of a surfcat is used, the surfcat is activated by the addition of a strong acid like HCl or $H_2SO_4$. The emulsion is allowed to polymerize either ambiently or by heating the vessel. Polymerization is halted by the addition of a base such as an amine, metal hydroxide, or metal carbonate.

The emulsion is then converted from an emulsion of silicone oil to a dispersion of silicone rubber via crosslinking by adding in a filler like colloidal silica, a crosslinker like a silane (optional), and an organotin catalyst. Methyltrimethoxysilane is a preferred silane. The organotin catalyst can be either a divalent tin or a tetravalent tin catalyst. The divalent tin catalyst may be any organotin with a 2+ oxidation state and organic ligands. Examples include tin(II) ethylhexanoate, tin(II) acetylacetonate, and tin(II) acetate. The tetravalent tin catalyst may be any organotin with a 4+ oxidation state, two covalently bonded organic groups and two ligands. Examples include dibutyltindilaurate, dibutyltindiacetate, and dioctyltindilaurate. The emulsion is then converted from an emulsion of silicone oil to a dispersion of silicone rubber via crosslinking by adding in a filler like colloidal silica, a crosslinker like a silane (optional), and an organotin catalyst. Methyltrimethoxysilane is a preferred silane. The organotin catalyst can be either a divalent tin or a tetravalent tin catalyst. The divalent tin catalyst may be any organotin with a 2+ oxidation state and organic ligands. Examples include tin(II) ethylhexanoate, tin(II) acetylacetonate, and tin(II) acetate. The tetravalent tin catalyst may be any organotin with a 4+ oxidation state, two covalently bonded organic groups and two ligands. Examples include dibutyltindilaurate, dibutyltindiacetate, and dioctyltindilaurate.

In certain embodiments, 99-100% of the linear monomers are converted into a polymer, and the polymerization takes 8-24 hours under ambient conditions.

The resulting product is an aqueous dispersion of crosslinked polydimethylsiloxane.

A third embodiment involves direct emulsification with no polymerization. In this method a linear, silanol terminated polydimethylsiloxane fluid similar to the second embodiment is used. However, the MW/viscosity of the starting fluid is much higher (10,000-100,000 cPs at 23° C.) and no polymerization takes place. No surfcat is used in the third embodiment, only a non-ionic surfactant(s).

The silanol fluid, surfactant(s), and water are emulsified.

The emulsion is then converted from an emulsion of silicone oil to a dispersion of silicone rubber via crosslinking by adding in a filler like colloidal silica, a crosslinker like a silane (optional), and an organotin catalyst. Methyltrimethoxysilane is a preferred silane. The organotin catalyst can be either a divalent tin or a tetravalent tin catalyst. The divalent tin catalyst may be any organotin with a 2+ oxidation state and organic ligands. Examples include tin(II) ethylhexanoate, tin(II) acetylacetonate, and tin(II) acetate. The tetravalent tin catalyst may be any organotin with a 4+ oxidation state, two covalently bonded organic groups and two ligands. Examples include dibutyltindilaurate, dibutyltindiacetate, and dioctyltindilaurate. The emulsion is then converted from an emulsion of silicone oil to a dispersion of silicone rubber via crosslinking by adding in a filler like colloidal silica, a crosslinker like a silane (optional), and an organotin catalyst. Methyltrimethoxysilane is a preferred silane. The organotin catalyst can be either a divalent tin or a tetravalent tin catalyst. The divalent tin catalyst may be any organotin with a 2+ oxidation state and organic ligands. Examples include tin(II) ethylhexanoate, tin(II) acetylacetonate, and tin(II) acetate. The tetravalent tin catalyst may be any organotin with a 4+ oxidation state, two covalently bonded organic groups and two ligands. Examples include dibutyltindilaurate, dibutyltindiacetate, and dioctyltindilaurate.

The resulting product is an aqueous dispersion of crosslinked polydimethylsiloxane.

Additives may be included with the aqueous silicone elastomer to formulate a final coating composition. Illustrative additives include fillers, pigments, binders, defoamers, rheology modifiers, or other additives common to paints.

For example, the aqueous silicone elastomer can optionally be mixed with at least one filler such as calcium carbonate, nepheline syenite, barium sulfate, diatomaceous earth, kaolin clay, pumice, etc.

The composition can be tinted any color by mixing the aqueous silicone elastomer with a pigment. For example, the aqueous silicone elastomer can optionally be mixed with titanium dioxide, or other white pigments, making the coating bright white. In another example the aqueous silicone elastomer can optionally be mixed with aluminum flake pigments making the coating silver.

The coating composition can also optionally include a binder. For example, the aqueous silicone elastomer can be blended with an organic, water-based binder such as an acrylic or a polyurethane. The acrylic or polyurethane binder can be an acrylic latex or a polyurethane dispersion that has a pH of >7. The amount of binder included in the composition may range from 5-30 wt %, based on the wet weight of the total composition.

In certain embodiments, the aqueous silicone elastomer in the final coating composition is present in an amount of 35-99 wt %, based on the wet weight of the total composition.

In certain embodiments, silicone is the only film-forming polymer present in the composition.

Topcoat for Underlying Roofing System

In one embodiment, the aqueous silicone elastomer-containing composition can be applied as a topcoat for an underlying roofing system. As used in this embodiment, "topcoat" means the final exterior surface of the roofing system that is in contact with the ambient atmosphere surrounding the building. In this embodiment, the coating composition is applied as a topcoat onto (i) a pre-existing membrane of a roofing system or (ii) the roof decking as weatherproofing for the building roof. The pre-existing membrane in embodiment (i) may be a single-ply roll on membrane or it may be a fluid-applied membrane such as a bituminous system. The roof decking in embodiment (ii) may be a structural or weight-bearing support structure (e.g., wood, metal, or composite beams, rafters, A-frames, etc.). The topcoat is the last applied layer, and provide an additional layer of weather protection, and are often white or silver (as described above) to reflect sunlight and reduce thermal heat gain.

The aqueous silicone elastomer-containing composition is applied to a roof system substrate as a liquid. Preferably, the liquid composition is sprayed onto the roofing system substrate. After application to the roofing system substrate the liquid dries to an elastomeric membrane.

The silicone-containing composition may be mixed with the other ingredients prior to use or dispensation and will form an elastomeric membrane upon the evaporation of water. Water is evaporated from the silicone-containing composition after the composition is applied to the substrate to form a silicone elastomer on the substrate. The evaporation of water may be performed under ambient, or atmospheric conditions at the location of the substrate. Alternatively, evaporation of water may be performed under artificially heated conditions, produced by one or more heaters.

The resulting silicone-containing membrane is substantially impervious to water. The silicone-containing membrane is resistant to degradation from weather (i.e., precipitation and wind), and remains flexible at both extremely low and high temperatures (e.g., −40° C. to 100° C.). The silicone-containing membrane protects the roof substrate below it from the deleterious effects of the exterior environment. The term "exterior environment" may refer to an environment characterized by a tropical/megathermal climate, a dry (arid and semiarid) climate, a temperate/mesothermal climate, a continental/microthermal climate, or a polar or alpine climate. The minimum application temperature may be down to −6° C. The drying time depends on the specific coating formulation and the applied coating thickness, but typically is 4 to 24 hours.

If formulated as a white or silver color, this membrane will also reflect sunlight and reduce the absorbed heat, lowering the HVAC costs of the building.

The dry membrane thickness may range from 3 to 30 mils, more particularly 3 to 15 mils.

In certain embodiments, only a single coating is required for forming the topcoat.

In certain embodiments, the coating method provides gap filling between 4×8 plywood sheathing.

Standalone, Complete Roofing System

In this embodiment, the aqueous silicone elastomer-containing composition is applied as a liquid over a roof substructure as the sole element of water and weather resistance for the roof system. In other words, the roofing system does not include any other waterproofing material. The roof substructure may be a structural or weight-bearing support structure (e.g., wood, metal, or composite beams, rafters, A-frames, etc.). Preferably, the liquid composition is sprayed onto the roof substructure. After application to the roof substructure, the liquid dries to an elastomeric membrane. The membranes is substantially impervious to water. The membrane is resistant to degradation from weather (i.e., precipitation and wind), and remains flexible at both extremely low and high temperatures (e.g., −40° C. to 100° C.). This provides water and weather-proofing for the roof.

Optionally, when applying the aqueous silicone elastomer-containing composition to the roof, chopped glass fibers may be added to the liquid via a chopper gun or similar method for added strength.

Optionally, after the aqueous silicone elastomer-containing coating has been applied to the roof, a construct (e.g., a woven mat) of glass fibers, polyester fibers or polyolefin fibers may be placed into contact with the liquid for added strength.

The aqueous silicone elastomer-containing composition will typically be applied in multiple coats to build up the required film thickness to form a standalone, complete roofing system. In certain embodiments, the dry total film thickness is 10 to 100 mils.

Optionally, a colored topcoat, such as white or silver, may be applied to the roofing film. This could be the aqueous silicone elastomer-containing topcoat as described above, or it could be another topcoat such as a conventional, commercially available acrylic or high solids silicone.

Optionally, the system could be topped with a single ply roofing membrane such as thermoplastic polyolefin (TPO) or ethylene propylene diene terpolymer (EPDM).

In view of the many possible embodiments to which the principles of the disclosed invention may be applied, it should be recognized that the illustrated embodiments are only preferred examples of the invention and should not be taken as limiting the scope of the invention.

What is claimed is:

1. A method comprising:
    onsite coating a liquid aqueous silicone elastomer-containing composition onto a surface of a building roof substrate, wherein the building roof substrate is an element of a standing building roofing system, and
    then drying the liquid aqueous silicone elastomer-containing composition resulting in forming a non-reinforced silicone elastomer-containing topcoat on the building roof substrate,
    wherein a water resistant barrier other than the silicone elastomer-containing topcoat is not present in the standing building roofing system.

2. The method of claim 1, wherein the topcoat has a dry thickness of 3 to 30 mils.

3. The method of claim 1, wherein the liquid aqueous silicone elastomer-containing composition further comprises a white color-imparting additive or a silver color-imparting additive.

4. The method of claim 1, wherein the coating comprises spraying of the liquid aqueous silicone elastomer-containing composition.

5. The method of claim 1, wherein the coating comprises roller coating of the liquid aqueous silicone elastomer-containing composition.

6. The method of claim 1, wherein the liquid aqueous silicone elastomer comprises a dimethyl siloxy silsesquioxane that is produced from ring opening polymerization of at least one cyclic siloxane monomer.

7. The method of claim 6, wherein the cyclic siloxane monomer is hexamethylcyclotrisiloxane, octamethylcyclotetrasiloxane, or decamethylcyclopentasiloxane.

8. The method of claim 6, wherein the dimethyl siloxy silsesquioxane has a molecular weight of 100,000 to 500,000 g/mol, and a viscosity of 100 to 500 cPs, at 23° C.

9. The method of claim 1, wherein the liquid aqueous silicone elastomer is produced from at least one linear polydimethylsiloxane that is terminated with at least one silanol group.

10. The method of claim 1, wherein the building roof substrate is a roof decking substrate.

11. The method of claim 10, wherein the roof decking is a structural or weight-bearing support structure.

12. The method of claim 1, wherein the aqueous silicone elastomer is the only film-forming polymer present in the composition.

13. The method of claim 1, wherein the aqueous silicone elastomer in the composition is present in an amount of 35-99 wt %, based on the wet weight of the total composition.

14. The method of claim 1, wherein the method is included in repairing and/or resurfacing of the standing building roofing system.

15. The method of claim 1, wherein the silicone elastomer-containing topcoat has a mass retention of at least 95% over a period of 2000 hours QUV, a gloss retention of at least 90%, over a period of 2000 hours QUV, and a color loss of less than one ΔE over a period of 2000 hours QUV.

16. A method comprising:
    onsite coating a liquid aqueous silicone elastomer-containing composition onto a surface of a building roof substrate, wherein the building roof substrate is an element of a standing building roofing system, and
    then drying the liquid aqueous silicone elastomer-containing composition to form a non-reinforced membrane on the building roof substrate, wherein the membrane is the only water and weather resistant element present in the standing building roofing system.

17. The method of claim 16, wherein the membrane has a dry thickness of 5 to 100 mils.

18. The method of claim 16, wherein the liquid aqueous silicone elastomer comprises a dimethyl siloxy silsesquioxane that is produced from ring opening polymerization of at least one cyclic siloxane monomer.

19. The method of claim 18, wherein the dimethyl siloxy silsesquioxane has a molecular weight of 100,000 to 500,000 g/mol, and a viscosity of 100 to 500 cPs, at 23° C.

20. The method of claim 16, wherein the liquid aqueous silicone elastomer is produced from at least one linear polydimethylsiloxane that is terminated with at least one silanol group.

21. The method of claim 16, wherein the aqueous silicone elastomer in the composition is present in an amount of 35-99 wt %, based on the wet weight of the total composition.

22. The method of claim 16, wherein the silicone elastomer-containing membrane has a mass retention of at least 95% over a period of 2000 hours QUV, a gloss retention of at least 90%, over a period of 2000 hours QUV, and a color loss of less than one ΔE over a period of 2000 hours QUV.

* * * * *